(12) United States Patent
Steinberg et al.

(10) Patent No.: US 11,854,124 B2
(45) Date of Patent: Dec. 26, 2023

(54) REAL-TIME PHOTOACOUSTIC IMAGING USING A PRECISE FORWARD MODEL AND FAST ITERATIVE INVERSE

(71) Applicant: The Board of Trustees of the Leland Stanford Junior University, Stanford, CA (US)

(72) Inventors: Idan Steinberg, Palo Alto, CA (US); Sanjiv Sam Gambhir, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 111 days.

(21) Appl. No.: 17/517,401

(22) Filed: Nov. 2, 2021

(65) Prior Publication Data
US 2022/0139004 A1    May 5, 2022

Related U.S. Application Data

(60) Provisional application No. 63/109,452, filed on Nov. 4, 2020.

(51) Int. Cl.
*G06K 9/00*     (2022.01)
*G06T 11/00*    (2006.01)
*A61B 5/00*     (2006.01)

(52) U.S. Cl.
CPC ......... *G06T 11/006* (2013.01); *A61B 5/0095* (2013.01); *G06T 2210/52* (2013.01); *G06T 2211/424* (2013.01); *G06T 2211/428* (2013.01)

(58) Field of Classification Search
None
See application file for complete search history.

(56) References Cited

U.S. PATENT DOCUMENTS 9,271,654 B2 * 3/2016 Razansky ............ A61B 5/0095

FOREIGN PATENT DOCUMENTS

WO    WO-2011025950 A2 *  3/2011  ........... A61B 5/0071

OTHER PUBLICATIONS

Azizian, Mohammad Kalkhoran, and Didier Vray. "Sparse sampling and reconstruction for an optoacoustic ultrasound volumetric hand-held probe." Biomedical optics express 10.4 (2019): 1545-1556.*

(Continued)

*Primary Examiner* — Emily C Terrell
*Assistant Examiner* — Owais Iqbal Memon
(74) *Attorney, Agent, or Firm* — LUMEN PATENT FIRM

(57) ABSTRACT

A method for photoacoustic imaging is performed by measuring RF time samples from transducer elements, and reconstructing an estimated initial pressure image from the measured RF time samples and a pre-calculated forward model matrix. The reconstructing involves minimizing the difference between the pre-calculated forward model matrix applied to the image estimate and the measured RF time samples by implementing a superiorized modified conjugate gradient least squares algorithm to minimize the total variation norm. The model matrix factors each of the transducer elements into sub-wavelength mathematical elements.

7 Claims, 13 Drawing Sheets

(56) References Cited

OTHER PUBLICATIONS

Azizian, Mohammad Kalkhoran, and Didier Vray. "Theoretical characterization of annular array as a volumetric optoacoustic ultrasound handheld probe." Journal of Biomedical Optics 23.2 (2018): 025004-025004.*

Kim, MinWoo, et al. "Deep-learning image reconstruction for real-time photoacoustic system." IEEE transactions on medical imaging 39.11 (May 2020): 3379-3390.*

Zibetti, Marcelo VW, Chuan Lin, and Gabor T. Herman. "Total variation superiorized conjugate gradient method for image reconstruction." Inverse Problems 34.3 (2018): 034001.*

Wang et al., A photoacoustic imaging reconstruction method based on directional total variation with adaptive directivity, BioMedical Engineering OnLine vol. 16, Article No. 64 (2017).

Azizian et al., Sparse sampling and reconstruction for an optoacoustic ultrasound volumetric hand-held probe, Biomedical Optics Express 10(4):1545. Mar. 2019.

Wang et al., Photoacoustic imaging reconsruction using combined nonlocal patch and total-variation regularization for straight-line scanning, BioMedical Engineering OnLine 17(1). Aug. 2018.

Mozaffarzadeh et al., Model-Based Photoacoustic Image Reconstruction using Compressed Sensing and Smoothed L0 Norm, Conference: Photons Plus Ultrasounds: Imaging and Sensing 2018. Feb. 2018.

Kong et al., Investigation on Reconstruction for Frequency Domain Photoacoustic Imaging via TVAL3 Regularization Algorithm, IEEE Photonics Journal, vol. 10 Issue: 5. Oct. 2018.

* cited by examiner

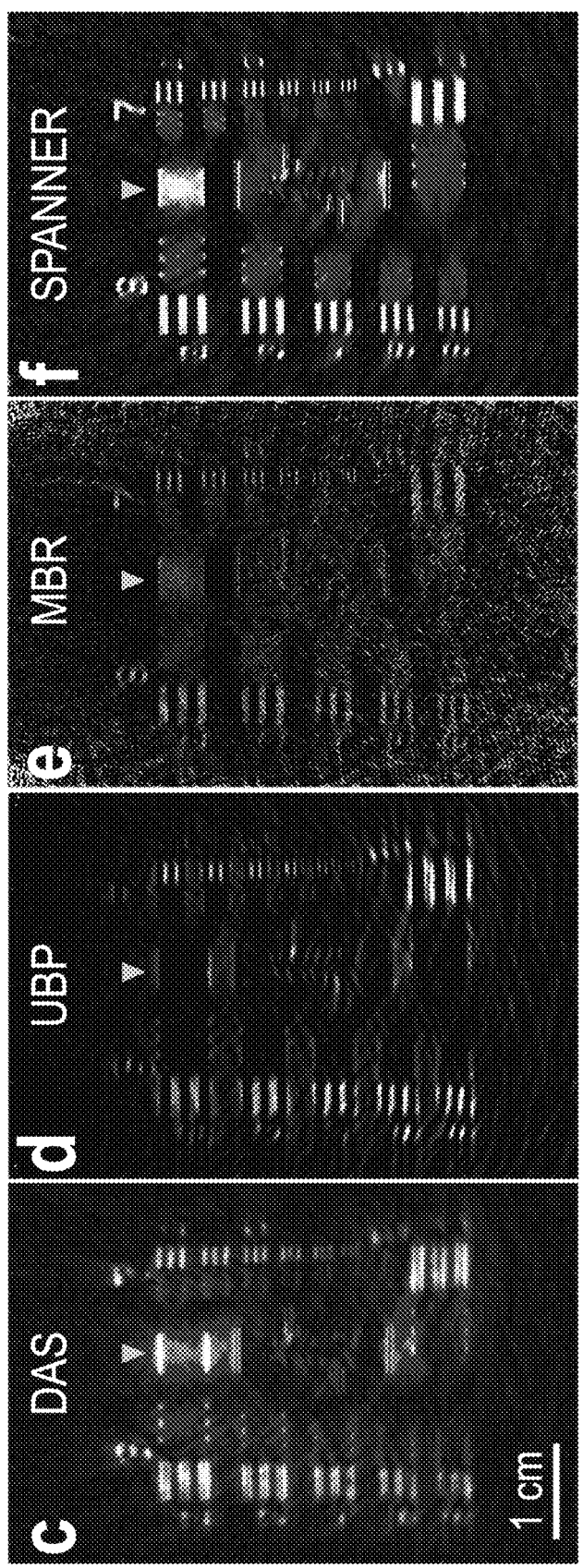
*Fig. 1C* *Fig. 1D* *Fig. 1E* *Fig. 1F*

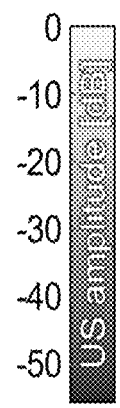

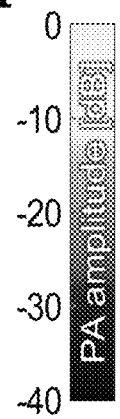

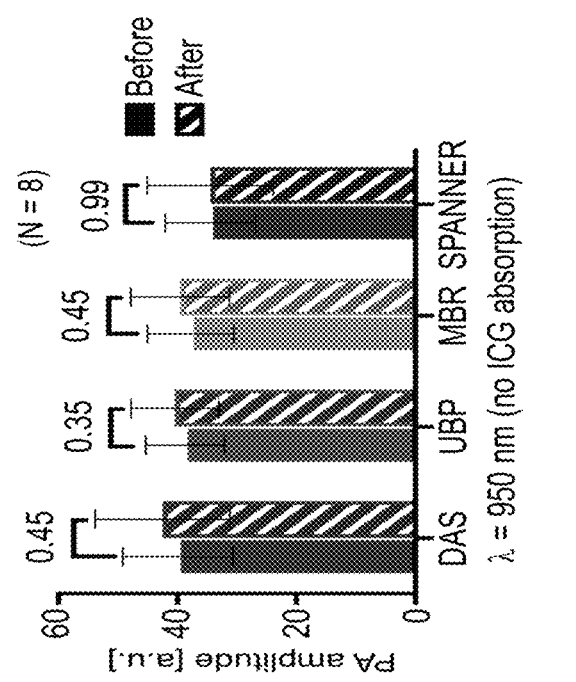
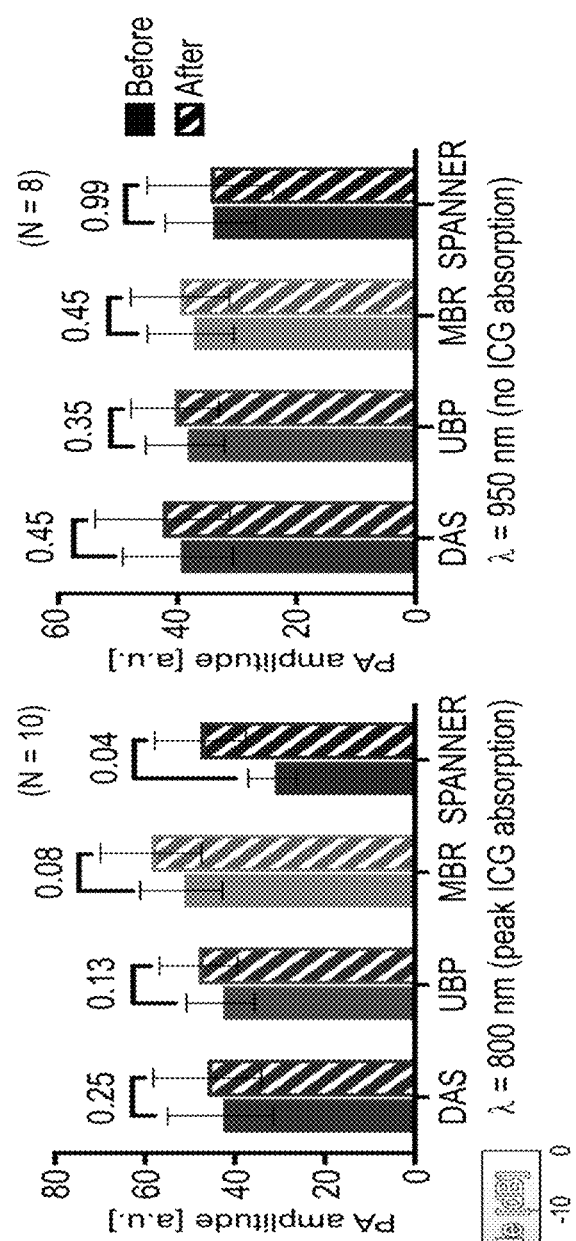
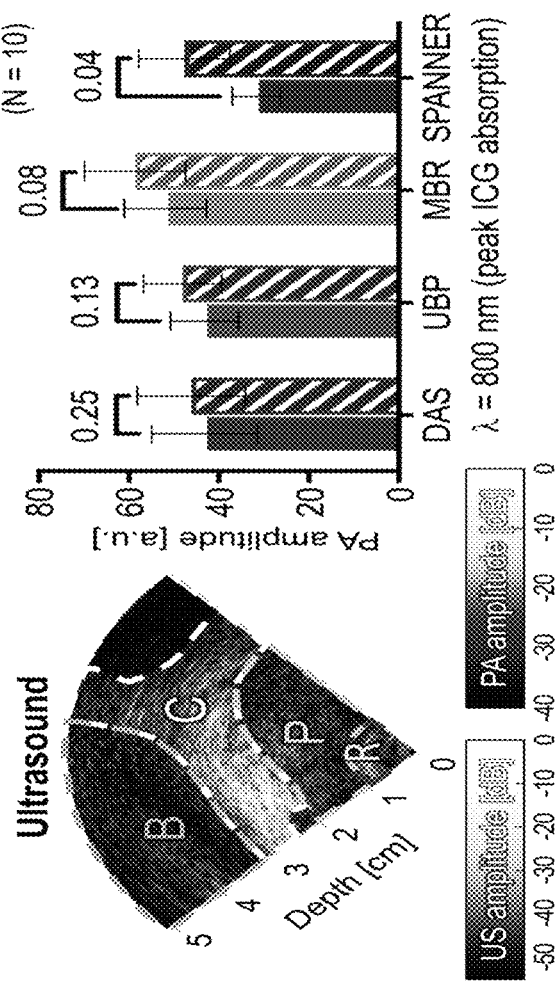

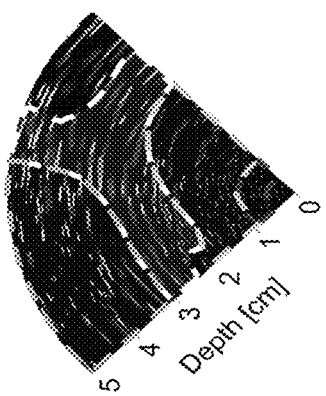
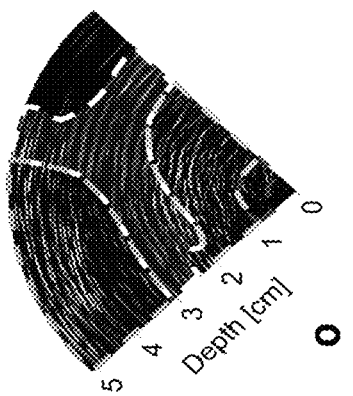
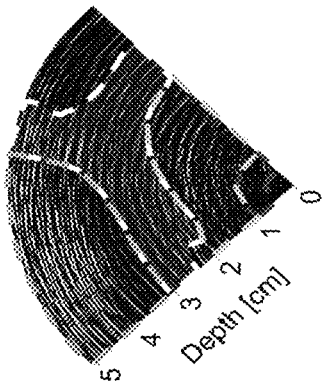
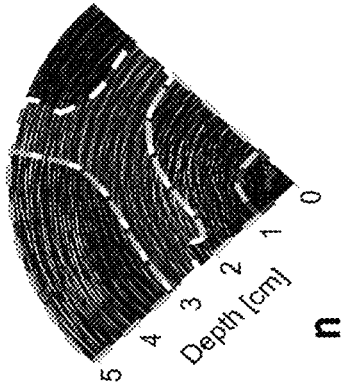
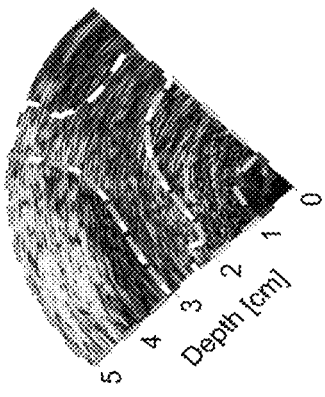
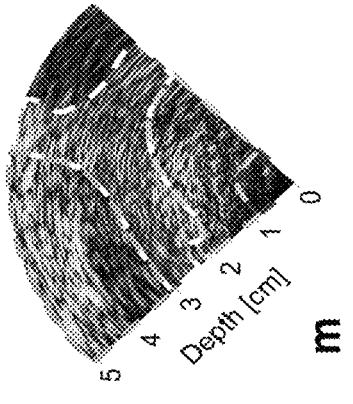
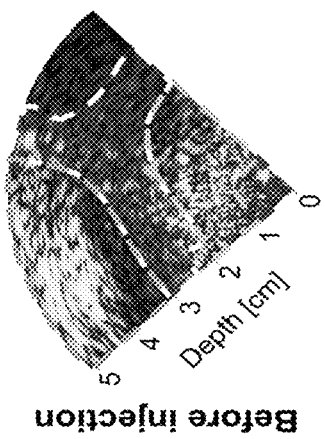
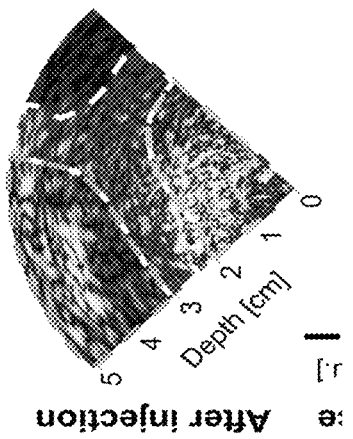
Fig. 5D  Fig. 5E  Fig. 5F  Fig. 5G
Fig. 5H  Fig. 5I  Fig. 5J  Fig. 5K

REAL-TIME PHOTOACOUSTIC IMAGING USING A PRECISE FORWARD MODEL AND FAST ITERATIVE INVERSE

CROSS-REFERENCE TO RELATED APPLICATIONS

This application claims priority from U.S. Provisional Patent Application 63/109,452 filed Nov. 4, 2020, which is incorporated herein by reference.

STATEMENT OF FEDERALLY SPONSORED RESEARCH

None.

FIELD OF THE INVENTION

The present invention relates generally to photoacoustic imaging techniques.

BACKGROUND OF THE INVENTION

Photoacoustic imaging (PAI), also known as optoacoustic imaging, is a biomedical imaging modality that combines the portability and high resolution advantages of ultrasound imaging (USI) with the molecular contrast and multiplexing capabilities of optical imaging methods[1, 2]. PAI derives its contrast from the optical absorption of tissues. PAI can be implemented in multiscale domains: either in a microscopy configuration[3], which sacrifices imaging depth to achieve micrometer scale resolution or in a tomographic configuration[4], which allows for a few centimeters of imaging depth with ultrasound resolution (typically sub-mm)[5]. Over the past twenty years, the engineering aspects of PAI were thoroughly researched with impressive results obtained mostly for phantom or small animal imaging[6-8]. More recently, clinical translation has begun with experimental clinical systems for thyroid cancers[9], lymph node metastasis[10], breast cancers, surgical guidance[11], psoriasis biomarkers[12], or carotid arteries[13]. PAI holds considerable promise for clinical translation with minimal interference to clinical workflow[14, 15] because it can be combined with conventional USI to provide co-registered anatomical and molecular information[16, 17].

The development of clinical, real-time photoacoustic imaging faces various technical challenges. Compared to common small animal preclinical imaging, real time clinical PA imaging requires greater imaging depth, fast imaging rate, higher signal-to-noise ratio, and the use of limited viewing angle while maintaining quantitative (or semi-quantitative) imaging. Available algorithms assume full-view detection and produce unacceptably high errors under realistic transducer configurations. This hurdle has prevented the practical utilization of photoacoustic in a clinical imaging system.

For many PAI technologies, the transition from full-body tomographic imaging in small-animal models to regional clinical human imaging, which allows illumination and detection from only one side, presents new challenges[18]. Such challenges include the limited viewing angles in the field of view, degraded signal-to-noise ratio (SNR) due to increased imaging depths, and a requirement for fast processing to allow real-time operation[19]. Moreover, co-registered high-quality USI is invaluable for clinical translation, as it is the standard of care for multiple procedures. Without a clear anatomical image, it is almost impossible to visually segment the image into clinically meaningful regions or find the same region of interest (ROI) in subsequent imaging sessions. Thus, the combination of USI and PAI might seem quintessential; the same transducer can serve as an acoustic emitter for USI as well as an acoustic receiver for both USI and PAI. However, those two modalities often pose different or even conflicting design requirements. USI utilizes small elements[20] (compared to the acoustic wavelength) and flat or convex transducer geometry, while PAI requires large area elements (to increase sensitivity) and concave or tomographic full view transducer geometries.

There remains an essential need for a clinical PAI system that can provide highly accurate and physically faithful image reconstruction in a sufficiently fast (typically 10-20 Hz) manner[18].

SUMMARY OF THE INVENTION

Described here is a new robust PAI reconstruction method called Superiorized Photo-Acoustic Non-NEgative Reconstruction (SPANNER), designed to reconstruct PA images in real-time. The method utilizes precise forward modeling of the PA propagation and reception of signals while accounting for the effects of acoustic absorption, element size, shape, and sensitivity, as well as the transducer's impulse response and directivity pattern. A fast superiorized conjugate gradient algorithm is used for inversion.

The invention provides a technique for real-time photoacoustic imaging which overcomes challenges of existing methods, allowing real-time photoacoustic imaging that is more quantitative. The photoacoustic image reconstruction method mitigates effects of limited viewing angles and high noise using a precise forward model of photoacoustic propagation and reception. The technique for real-time photoacoustic imaging uses a precise forward model of propagation and reception to improve the contrast of endogenous factors (such as increased vascularity or decreased oxygen saturation hypoxia) or exogenous agents. Specifically, the forward model matrix factors each transducer element into sub-wavelength mathematical elements, thus accounting for its 3D shape. A superiorized modified conjugate gradient algorithm is used for real-time inversion of model relations.

The PAI technique can be combined with ultrasound imaging to provide both ultrasound anatomical data and molecular information based on light absorption. For example, a dual ultrasound and photoacoustic imaging system can provide real-time transrectal imaging of the prostate. Such a system can be used for imaging both anatomy via ultrasound and molecular contrast via photoacoustic imaging. A regular transrectal ultrasound device may be combined with integrated photoacoustic imaging to achieve a much higher contrast regarding blood oxygenation, hemoglobin content. The contrast can be even improved by the injection of an FDA approved dye (ICG). This may be used predominantly for assessing the performance of the device and the ability to integrate it with a standard clinical diagnosis of prostate cancer. The combined system can be used as a regular transrectal ultrasound system, and because of the included photoacoustic imaging capability, it enables a much higher contrast of endogenous and exogenous agents. The better contrast allows physicians to take more accurate biopsy samples and improve guided surgery.

Prior work has combined photoacoustic and ultrasound imaging modalities, but none has been successful at real-time hybrid imaging with high quality. For example, Azizian et al. "Sparse sampling and reconstruction for an optoacoustic ultrasound volumetric hand-held probe" teaches a method to improve the reconstruction of a photoacoustic image. However, the purpose of Azizian et al. is to compensate for missing or removed transducer elements due to sparse sampling. Thus, the data of the missing intermediate channels are contained within the adjacent existing channels and needs to be recovered. Moreover, the application of compensating for missing transducer elements is very much limited to sparse transducers, which are not the standard of care. In contrast, the technique of the present invention improves imaging depth, SNR, and fidelity by (partially) recovering data beyond the scope of the current transducer channels, and thus it can be thought of as an extrapolator rather than an interpolator. This application is much broader and applies to any photoacoustic imaging system.

In addition, the algorithm used by Azizian is an offline algorithm, running on the CPU and intended as a design tool and a way to improve results even in the absence of some of the channels. In contrast, the technique of the present invention is a real-time algorithm, running on the GPU and intended for clinical use with a photoacoustic system during various procedures.

Also in contrast with the technique of the present invention, the model matrix by Azizian et al. does not factor each transducer element into sub-wavelength mathematical elements, it does not account for individual element sensitivity and only indirectly includes data regarding each element's directivity and shape. Thus, it is less accurate and harder to apply to a real-life transducer.

A key difference compared to Azizian and all prior work cited is that the techniques of the present invention are capable of providing real-time imaging and are not limited to offline image reconstruction. This is extremely important for clinical imaging. Prior techniques are limited to small animals/phantoms, where the whole region of interest can be surrounded with detectors, the data recorded, and then processed offline. On the contrary, in clinical photoacoustic imaging with a handheld probe, the clinician needs to be provided with immediate visual feedback.

Thus, the methods of the present invention provide great value and application compared to other model-based methods that are not fast enough for real-time imaging.

Other model-based methods do not have a model matrix that factors each transducer element into sub-wavelength mathematical elements, thus accounting for its 3D shape. As a result, they are much less efficient.

Other model-based methods do not account for individual element sensitivity or include data regarding each element's directivity. As a result, they are less efficient.

To evaluate the performance of the SPANNER technique of the present invention, it is experimentally compared to three existing reconstruction algorithms: delay-and-sum (DAS), universal back-projection (UBP), and model-based reconstruction (MBR). All four algorithms are applied to both simulations and experimental data acquired from tissue-mimicking phantoms, ex vivo tissue samples, and in vivo imaging of the prostates in patients. Simulations and phantom experiments highlight the ability of SPANNER to improve contrast to background ratio by up to 20 dB compared to all other algorithms, as well as a 3-fold increase in axial resolution compared to DAS and UBP. Applying SPANNER on contrast-enhanced PA images acquired from prostate cancer patients yielded a statistically significant difference before and after contrast agent administration, while the other three image reconstruction methods did not, thus highlighting SPANNER's performance in differentiating intrinsic from extrinsic PA signals and its ability to quantify PA signals from the contrast agent more accurately.

In one aspect, the invention provides a method for photoacoustic imaging comprising measuring RF time samples from transducer elements, and reconstructing an estimated initial pressure image from the measured RF time samples and a pre-calculated forward model matrix. The reconstructing comprises minimizing the difference between the pre-calculated forward model matrix applied to the image estimate and the measured RF time samples by implementing a superiorized modified conjugate gradient least squares algorithm to minimize the total variation norm. The model matrix factors each of the transducer elements into sub-wavelength mathematical elements.

The method may be implemented using photoacoustic transducer elements that produce RF time samples, and a processor that reconstructs a photoacoustic image from the RF time samples. The method may be implemented with a combined ultrasound and photoacoustic transducer to implement the photoacoustic imaging in combination with ultrasound imaging.

BRIEF DESCRIPTION OF THE DRAWINGS

FIGS. 1C, 1D, 1E, 1F are images reconstructed using DAS, UBP, MBR, and SPANNER reconstruction methods.

FIG. 5A is a B-mode ultrasound image including rectal wall (R), prostate (P), connective tissue (C), and bladder (B).

FIGS. 5B, 5C are bar graphs illustrating Quantified PA amplitudes at the prostate before and after injection of ICG at 800 nm and 950 nm, respectively.

FIGS. 5D, 5E, 5F, 5G are pre-injection PA images reconstructed using DAS, UBP, MBR, and SPANNER reconstruction methods.

FIG. 5H, 5I, 5J, 5K are post-injection PA images reconstructed using DAS, UBP, MBR, and SPANNER reconstruction methods.

DETAILED DESCRIPTION OF THE INVENTION

Figure 1A:
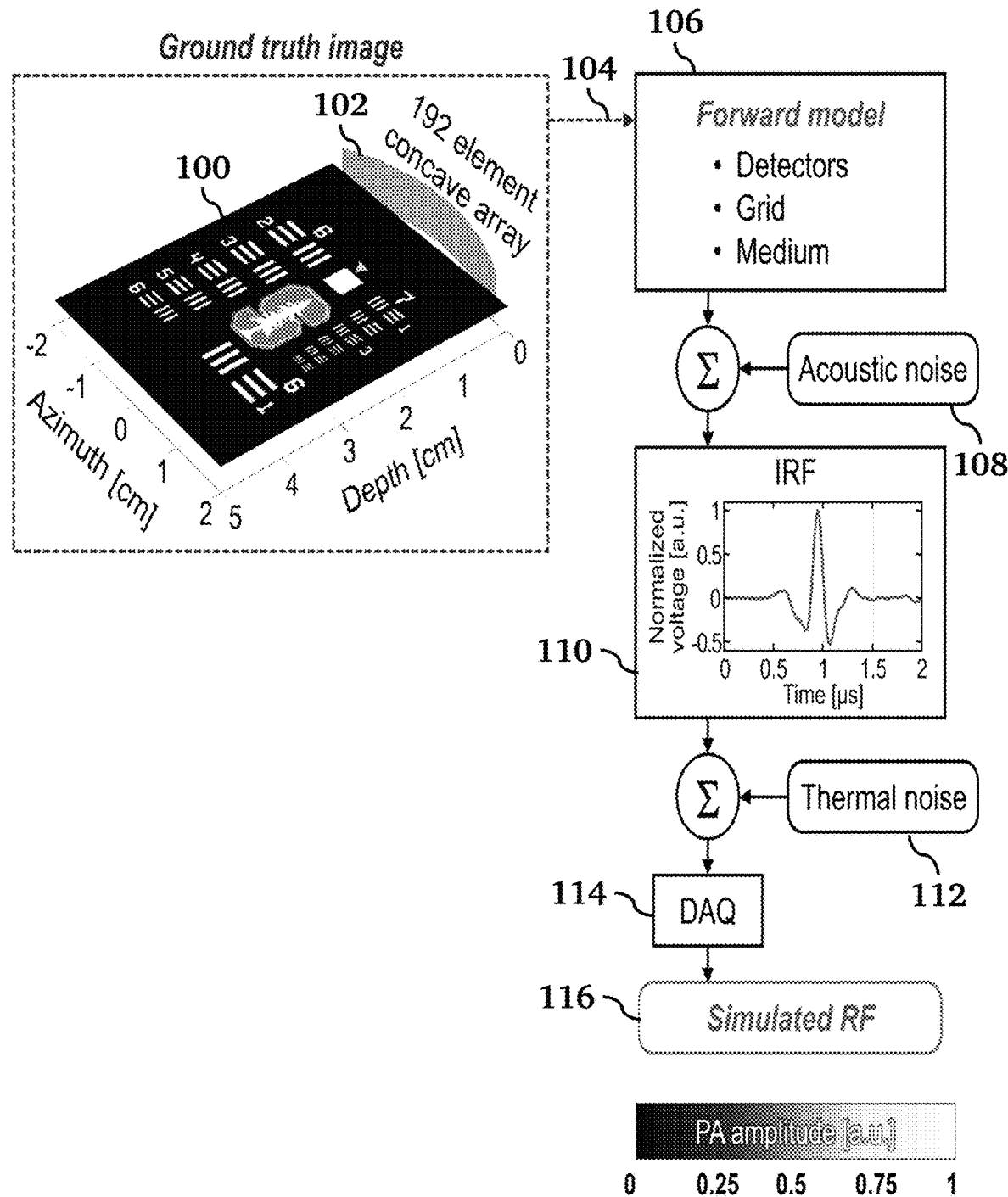
FIG. 1A is a schematic diagram illustrating an overview of processing pipeline for generating a simulated RF signals from a ground truth image using a forward model, according to an embodiment of the invention.

Here, we describe and demonstrate a reconstruction technique, Superiorized Photo-Acoustic Non-Negative Reconstruction (SPANNER), that provides high quality real-time photoacoustic (PA) image reconstruction even in the presence of limited view and low SNR. This PAI reconstruction method uses the concept of mathematical superiorization [21] and is achieved using a detailed model matrix for forward modeling, as well as a superiorized and modified conjugate gradient algorithm for real-time inversion of the model relations. The SPANNER technique is compared to the two most common image reconstruction algorithms: delay-and-sum (DAS) and universal back-projection (UBP) [22]. Moreover, to distinguish the contribution of the SPANNER algorithm from the contribution of the forward model-matrix, we compare it with a model-based reconstruction (MBR) scheme based on a regularized typical least-squares solver[23].

The SPANNER Algorithm

We begin with a presentation of a model of the PA reconstruction problem. The goal of PA image reconstruction method is to find $\hat{p}$, an estimated initial pressure image, given s, a vector of all the measured RF time samples from all detectors, and M, a pre-calculated forward model matrix that transforms the unknown true image p into noiseless RF samples: s=Mp. Additional a-priori constraints are added to the reconstruction in lieu of the missing data to negate the effects of noise and limited view. Regardless of the image content, a high-quality PA image should ideally exhibit only nonnegative physical values, clear boundaries, and no signals from optically non-absorptive regions. Thus, proper constraints and regularization are essential for better image quality. In particular, the anisotropic $L^1$ total variation (TV) regularization is adapted to enforce desirable image features. TV demonstrates superior performance over classical regularizations[24] since sharp edges are preserved but are not necessarily under- or over-expressed compared to the smooth ones. Instead, the presence of these edges hinges upon the detected signals. However, a non-differentiable $L^1$ regularization scheme poses challenges for implementation and integration with a conjugate gradient type algorithm. These challenges are exacerbated in a real-time algorithm, where computation efficiency is critical. Thus, the present technique uses superiorization to perturb a non-linear conjugate gradient algorithm. Superiorization techniques are typically used to improve the efficacy of iterative algorithms in which convergence is resilient to perturbations[21]. Leveraging upon such algorithmic resilience, perturbations can be utilized to steer the algorithm's iterations away from the path that the original algorithm would naively take. The perturbed algorithm is often called the 'superiorized version' of the original unperturbed algorithm. These perturbations force the superiorized algorithm to produce the results that have more desirable attributes compared to the original algorithm, even in the presence of partial or noisy data. Adapting techniques in the work of Zibetti et al[25], we perturbed the non-linear conjugate gradient algorithm to produce a nonnegative, total variation regularized, rapidly converging result. Thus, the problem to be solved for every frame is characterized as follows:

$$\hat{p}_{SPNR} = \underset{\tilde{p} \geq 0}{\operatorname{argmin}} \{ \|M\tilde{p} - s\|_2^2 + \|\lambda \tilde{p}\|_2^2 + TV(\tilde{p}) \} \quad (1)$$

where $\tilde{p}$ is the initial pressure, M is the model matrix, s is the raw pressure waveform, and $\lambda$ is a scalar parameter to control the regularization. The notation $\|\bullet\|_2$ denotes the $L_2$ norm while TV($\bullet$) denotes the total variation norm. Additionally, a precise model matrix is constructed. Succinctly, the elements of the model matrix M equal the photoacoustic signal from the $i^{th}$ detector element $s_i$ at the $k^{th}$ time step (with recorded signal length of K samples) as a response to a Dirac delta pressure source at the $j^{th}$ pixel $p_0^{(j)}(r)$:

$$M[k + iK, j] = s_i(t_k \mid p_0^{(j)}) = \quad (2)$$

$$\frac{\Gamma A_i}{4\pi v_s} \left\{ \iiint_{\|r-d_i\|_2 = v_s t_k} \exp\{-\alpha \|r - d_i\|_2 f_c\} D_i(r - d_i) \frac{\Omega_i(r) * p_0^{(j)}(r)}{\|r - d_i\|_2} dr \right\} * \frac{\partial h_i(t)}{\partial t}$$

where $\Gamma$ is the Grüneisen coefficient, $f_c$ is the detector's central frequency, $v_s$ is the speed of sound in the imaged medium, and a is the acoustic attenuation (in Nepers per unit distance per unit frequency). Each non-ideal detector, is characterized by its location $d_i$, its directivity function $D_i(\bullet)$, its surface $$\Omega_i(r) = \begin{cases} 1 & r \in \text{detector area} \\ 0 & \text{otherwise} \end{cases}$$

its sensitivity $A_i$, and its impulse response $h_i(t)$.

By using a two dimensional Cartesian grid and bilinear interpolation, the relation in Eq. 2 can be written in a vector-matrix form. This implementation deviates from the one presented by Rosenthal et al. [26-28] in the sense that it accounts for the medium properties, the individual element properties of each detector in advance without the need to constantly re-calculate these on the fly. Finally, the use of a Cartesian grid rather than a triangular grid allows more efficient computation of the total variation regularization.

Overall, SPANNER allows a rapid convergence rate on the order of tens of milliseconds on a graphics processing unit (GPU). Further reduction in computation time is achieved by several techniques: a) parallel implementation of the algorithms on the GPU, b) use of the Jian, Han & Jiang hybrid coefficient[29] to incorporate computed data from previous iterations to accelerate the next iteration, c) incorporation of data from previous reconstructed images as an initial guess for the algorithm to accelerate the reconstruction of the next image (i.e., hot-start), and d) normalization of the model matrix columns, which is known to accelerate numeric algorithms.

Methods

In Silico Evaluation

A controlled simulation environment with a well-characterized ground truth was used to compare the DAS, UBP (as implemented in ref [22], Section VI), MBR, and SPANNER reconstruction methods. FIG. 1A shows the simulated phantom and the forward generation of RF. A concave array 102 is used to image the target 100 from only one side. Forward simulation steps were taken for generating the simulated RF signals 116 from the ground truth image 104.

We simulated a 192-element concave array 102 with a 200-micron pitch and 6 mm height. The simulated target 100 was a scaled United States Air Force (USAF) target with an added Stanford University logo in the center. A forward model matrix 106 was calculated based on the imaging grid (5 cm in depth and 4 cm in azimuth with a 150-μm resolution), acoustic properties of the medium (e.g., speed of sound of 1540 m/s, acoustic attenuation of 0.5 dB/MHz/cm, and Grüneisen coefficient of 0.15), and the detector properties (such as shape, directivity, and sensitivity). In the forward simulation steps to generate RF data, the model matrix 106 was applied to the ground truth image 104, and gaussian white noise 108 was added. Then, each channel was filtered 110 with a 80% bandwidth impulse response function (IRF). This simulated both the effect of the impulse response and in-band noise. Additional white noise 112 was added, and the data was quantized 114 at 14-bit levels to produce the simulated RF 116. The noise spectral power was varied with respect to the signal power to achieve the desired SNR. Pre-processing for all algorithms included a Wiener deconvolution filter acting on the noisy RF waveforms. In post-processing, nonphysical negative reconstruction values were set to zero for the UBP and MBR algorithms, but no further post-processing steps were taken. The reconstruction performance of each algorithm was evaluated as a function of input RF data SNR, ranging from −9 dB to 20 dB in increments of 3 dB. For each noise level, a total of 200 simulations were performed using random images and noise values. The location of the absorbing pattern was randomly shifted inside the ROI and flipped in both directions to generate different images. Each simulation contained a different realization of random noise, scaled to maintain the specified SNR. The performance was quantified using the root mean square error (also known as the $L^2$ norm) with respect to the noiseless ground truth image. For each noise level, the mean error and 95% confidence intervals were calculated.

In Vitro Characterization

Figure 2A:
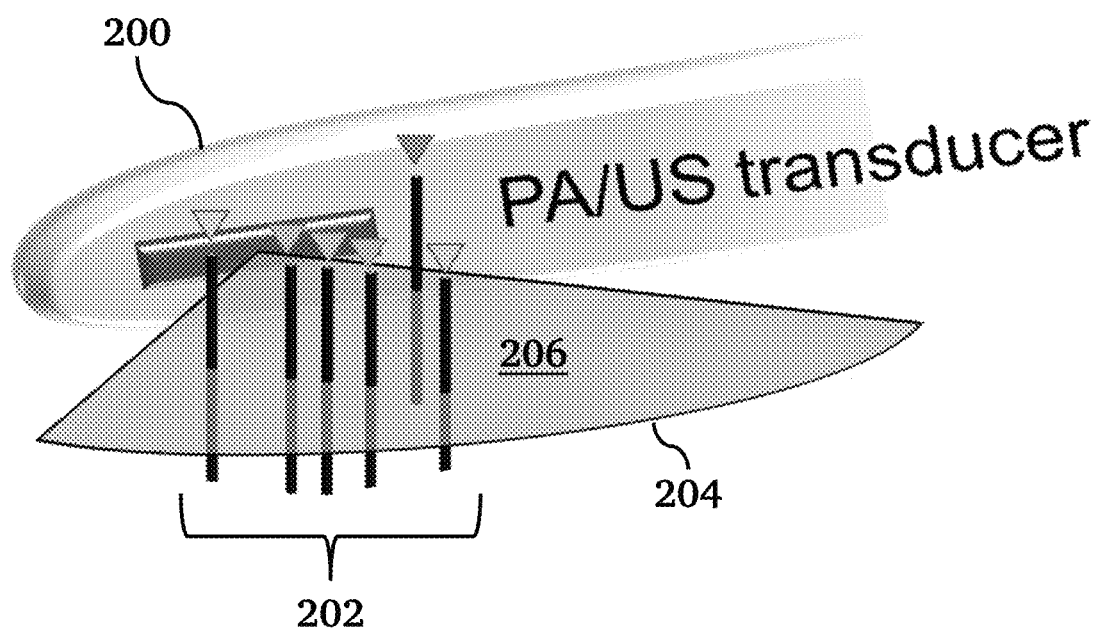
FIG. 2A depicts an experimental setup of a photoacoustic and ultrasound transducer and wires being imaged.

All algorithms were first evaluated in data previously acquired using a prototype PAI device[30, 31] with a single optical wavelength of 750 nm. The PA signals were acquired using a linear array transducer with 64 elements and a total aperture length of 12.8 mm. The subtended viewing angle at clinically-relevant depths is 65° at 1 cm depth and decreases to less than 15° at 5 cm depth. The impulse response and sensitivity varied greatly between channels and were estimated based on the RF data itself. These were then incorporated into a Weiner-filter pre-processing stage, as well as into the model matrix used by the MBR and SPANNER algorithms. Additionally, the effect of the time-gain-compensation curve was removed during pre-processing from the raw RF data to achieve a constant gain at all depths, as defined by the average intensity across the lateral span. Six black fishing wires (100 micron in diameter) perpendicular to the imaging plane were immersed in water (FIG. 2A). The DAS, UBP, MBR, and SPANNER images were reconstructed from data with identical pre-processing, and the axial resolution was measured as the full-width at half maximum (FWHM).

To test the multispectral performance of the SPANNER, we have reanalyzed RF data obtained from a chicken breast phantom experiment[46]. Two pieces of chicken breast (1.8 cm in thickness) were used to sandwich a microcentrifuge tube containing indocyanine green (ICG) dissolved in PBS at 1.3 mM. PA images were acquired with optical excitation wavelengths ranging from 750 to 950 nm. The amplitude values across the tube were calculated and normalized with respect to the laser power, as well as the adjacent chicken breast surroundings (5 mm below and above the ICG tube) to negate the effect of spectral coloring. The mean and 95% confidence intervals were value calculated as a function of the optical excitation wavelength.

Ex Vivo Imaging of Pancreatic Cancers

We reconstructed the PAI data that was previously collected and analyzed during a clinical trial reported by Tummers et al[47]. In this study, a small cohort of patients (N=7) were injected with 50-100 mg of a functionalized fluorescent agent (panitumumab-IRdye800), which is targeted to the EGFR receptor expressed in pancreatic carcinomas. The confirmed pancreatic cancer patients were injected with the imaging agent 2-5 days prior to fluorescent-guided tumor resection. This period allowed proper agent accumulation at the tumor sites and clearance of the free dye. Following the surgeries, the freshly resected pancreas samples were scanned with both a fluorescence imaging (FLI) system, as well as a custom made PAI system previously reported by our group[46]. Both the FLI and PA images were then correlated to assess the potential of using those modalities for real-time surgical guidance. To ensure the integrity of the samples, they were sandwiched between two agar blocks.

In Vivo Imaging of Prostate Cancer Patients

Finally, we assessed the efficacy of these algorithms in reconstructing in-vivo PAI data, which were collected using the same device[30]. In this study, PAI RF data were collected from ten patients with suspected prostate cancer lesions who were scheduled for a standard-of-care ultrasound-guided prostate biopsy. These patients were scanned with multiple optical excitation wavelengths (700 nm to 950 nm with a 25 nm interval) before and after systemic injection of FDA-approved ICG contrast agent with doses of 5 to 75 mg in a single bolus injection. Kothapalli et al[46] have recently reported the complete details of this study. Despite the large doses of ICG, the PA images produced in the original work could not demonstrate a statistically significant difference between the images pre- and post-injection (p>0.57 at 800 nm) without resorting to a complicated multi-region, multispectral analysis based on linear unmixing of hemoglobin and ICG. Accurate spectral unmixing remains a significant challenge in PAI[32] due to the absence of multispectral optical fluence compensation[33]. This problem is exacerbated when long measurement times (10-20 minutes per session) introduce motion artifacts and when low SNR and narrow viewing angles skew the reconstruction. Thus, under such conditions, spectral unmixing is inaccurate. To avoid this problem, we chose to focus on a single wavelength of 800 nm close to the ICG peak absorption spectrum (around 790 nm, concentration-dependent). Only the very last image acquired before and immediately after injection were compared. To make the analysis more clinically relevant and to reduce motion artifacts further, we delineated the prostate region in each image manually and quantified the PA signals within the prostate. Then, we used a threshold to reject the lower 10% values within the prostate, thus highlighting blood vessels and regions with high absorbance. We used a two-tailed, paired t-test between the pre- and post-injection images to determine statistical significance. To further assess if the signal increase observed post-injection is attributed to ICG injection and not to any intrinsic contrast or motion artifacts, we analyzed the PA images acquired at 950 nm excitation. Since ICG does not absorb light at 950 nm[34], the images pre- and post-should be statistically equivalent. There are multiple statistical tests to affirm statistical equivalency. The simplest is by using one set of the full overlap of the entire 90% confidence intervals pre- and post-injection to test each reconstruction's ability to quantify a lack of change. For a fair comparison, the PA images presented from this study were jointly normalized to a 40 dB range for both pre- and post-injection images, the amplitude of the PA signal is presented with respect to the maximal amplitude post-injection with the same optical excitation wavelength of 800 nm. All analyses were performed on the linear scale values. Finally, we analyzed the PA amplitude as a function of the ICG dose injected into each patient. As the signal value changes significantly from patient to patient, we calculated the ratio (i.e., mean PA amplitude in the prostate post-injection divided by the same amplitude pre-injection). These ratios were plotted (best fit and 90% prediction bounds) as a function of the dose for each of the four algorithms.

GPU Implementation of SPANNER

Implementation of the SPANNER method uses heavy computations for real-time operation. Simultaneous co-localized USI and PAI were implemented for GPU-based execution on a single high-end GPU (Nvidia, Quadro GV-100, USA) based on a modified open-source GPU beamforming package by Hyun et al[35]. USI was performed using a diverging-beam, coherently compounded synthetic aperture sequence, and PAI was performed using the SPANNER algorithm. The algorithm was implemented as a set of CUDA kernels based on cuBLAS-V2 and cuSPARSE libraries. Computations were further accelerated by using the Jian, Han, & Jiang hybrid coefficient[29] to incorporate computed data from previous iterations to speed up the next iteration, and by using previously-reconstructed images as an initial guess for the algorithm to accelerate the reconstruction of the following image (i.e., hot-start). Finally, an optional pre-processing step of frequency Wiener filtering was implemented in the frequency domain using the cuFFT library for Fast Fourier Transforms. The CUDA implementation also normalized and log-compressed the images as necessary as well as extracted timestamps and maximal values for both PA and US images.

Results

Figure 1B:
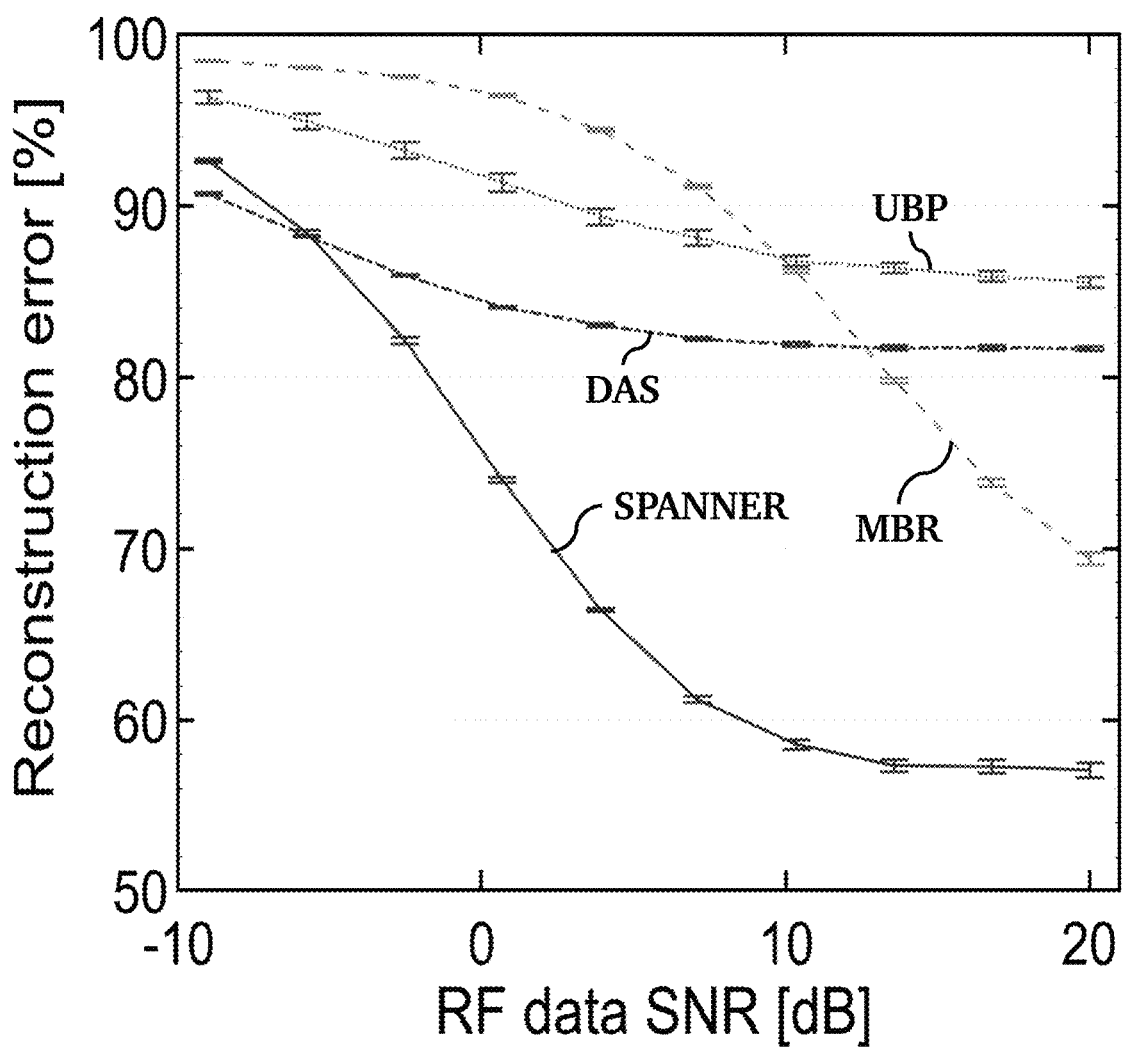
FIG. 1B is a graph illustrating a comparison of the reconstruction performance of three algorithms as a function of different SNR of the input RF data.

Due to the limited view angle, spatial frequencies in the azimuthal direction cannot be fully recovered by any of the algorithms. As expected, all algorithms performed better as the SNR of the input RF data increases. However, as the SNR improves, the artifacts due to the limited view become dominant and hamper further reduction in the reconstruction error. FIG. 1B shows a comparison of the reconstruction performance of the three algorithms as a function of different SNR of the input RF data. The error is shown with respect to a random guess reconstruction. For each noise level, the average error and 95% confidence intervals are shown. The graph shows the RMS reconstruction errors compared to the ground truth image. The error was normalized with respect to the error from a random guess. The SPANNER produces the most accurate result for the most input noise levels. Accuracy is improved up to 3-fold compared to DAS and UBP at the high SNR and up to 7-fold compared to MBR at the low and mid-range SNRs.

FIGS. 1C, 1D, 1E, 1F shows image reconstructions using DAS, UBP, MBR, and SPANNER reconstruction methods. Triangles mark a region of interest in the upper central region of each image. The DAS algorithm severely smears the image, and the image values are not quantitative as the lower spatial frequencies (i.e., the baseline) are missing. This means that the pixel values do not scale with the actual absorption. One can observe that the full rectangle in the upper region (marked with a triangle) appears as two boundaries with minimal signal inside, instead of accentuating the proximal and distal edges. The UBP algorithm exhibits much less smearing in the axial direction but still fails to reconstruct the lower frequency content. While the MBR was able to achieve a more quantitative reconstruction close to the detector array, it is severely hampered by the noise, and the reconstructed image is very unclear at depth. In contrast, the SPANNER was able to reconstruct both clear boundaries and preserve the feature's inner filling accurately, although there is some smearing in the lateral direction.

In Vitro Characterization

Figure 2B:
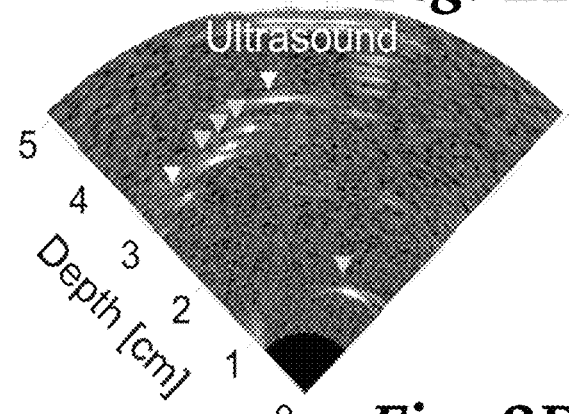
FIGS. 2B, 2C, 2D, 2E, 2F show images generating using, respectively, a conventional B-mode ultrasound method, DAS, UBP, MBR, and SPANNER methods.
Figure 2C:
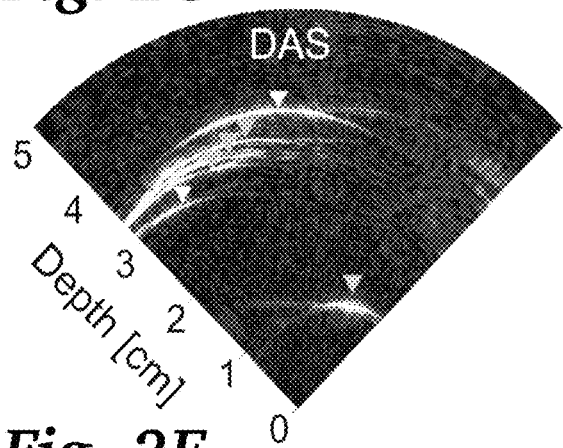
Figure 2D:
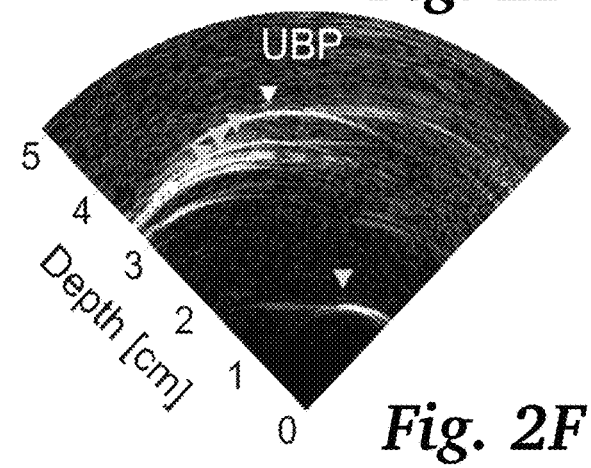
Figure 2E:
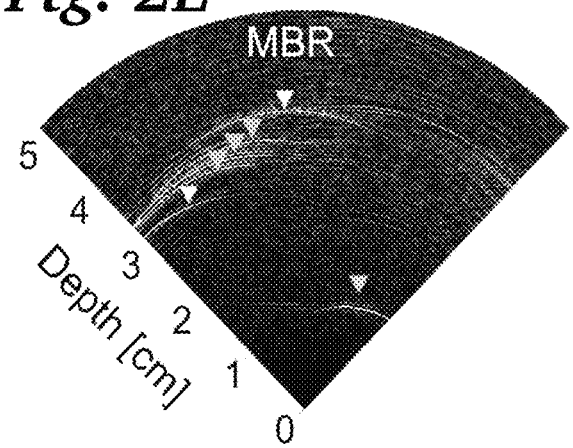
Figure 2F:
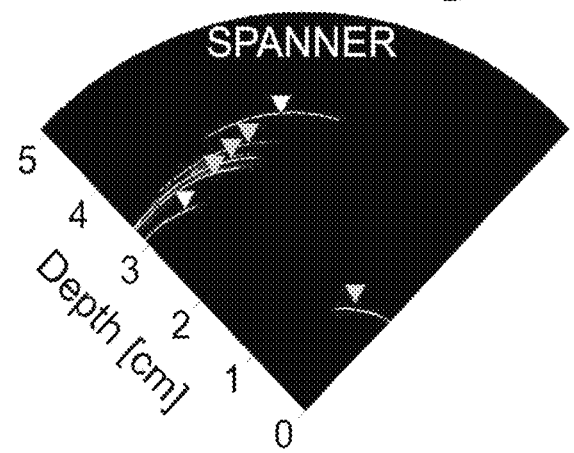

FIG. 2A depicts the experimental setup used for in vitro imaging using a single optical wavelength. A PA/US transducer 200 with field of view 206 is used to image six black fishing wires 202 (100 micron in diameter) immersed in water and oriented perpendicular to the imaging plane 204. FIG. 2B shows a conventional B-mode ultrasound image of the wires, each marked in the image with a triangle. The reconstructed images produced by DAS, UBP, MBR, and SPANNER algorithms are shown in FIGS. 2C, 2D, 2E, 2F, respectively. Both DAS and UBP demonstrate low resolution (both axial and lateral) and a high background noise clutter (i.e., spurious signals). The MBR algorithm also suffers from a high spurious background. While the SPANNER algorithm could not improve the lateral resolution, it had a much higher axial resolution and improved the signal to background ratio.

Figures 2G, 2H:
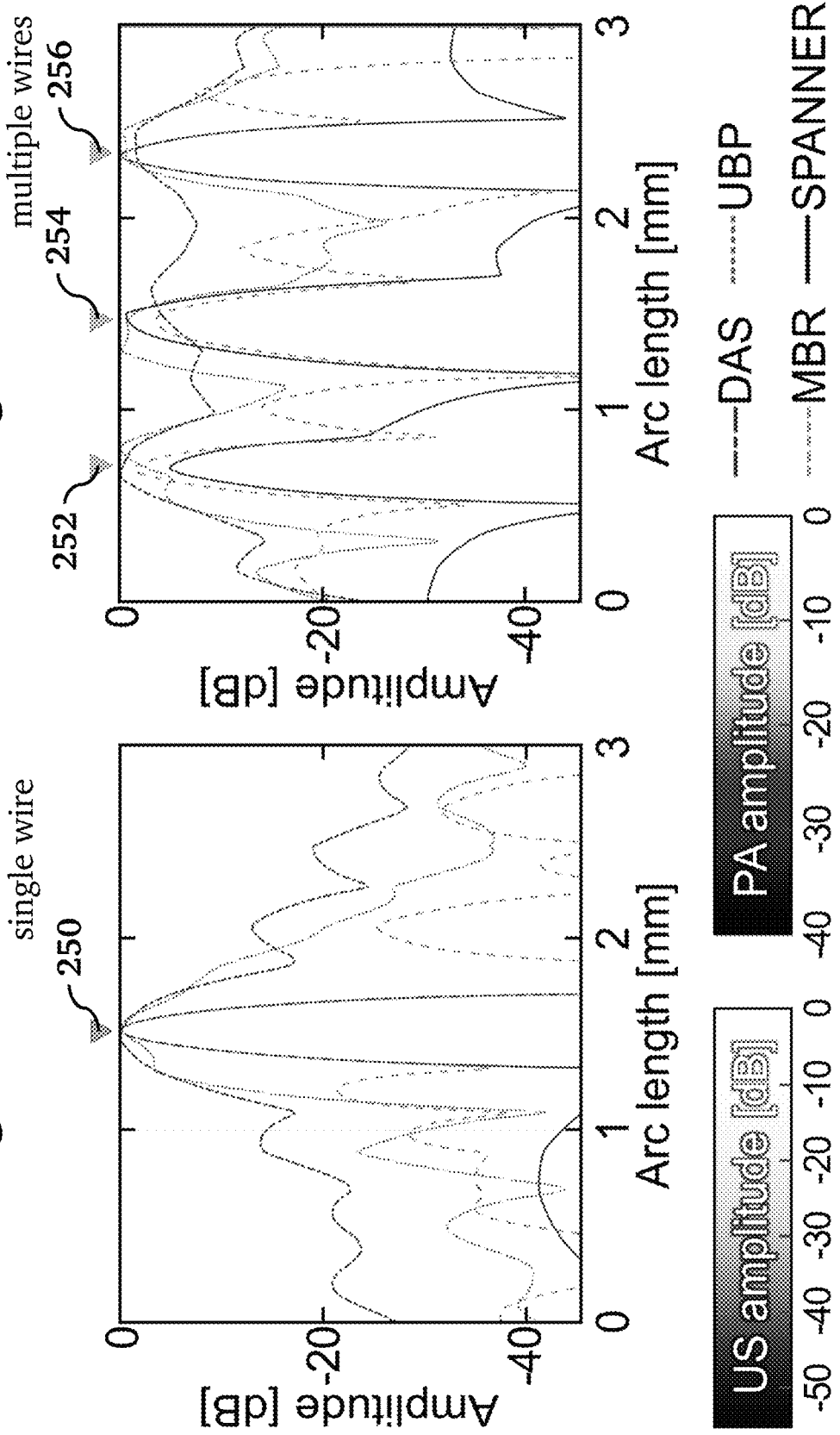
FIGS. 2G, 2H are graphs showing amplitude profiles along a single wire and multiple wires, respectively.

FIG. 2G, 2H show cross-sectional PA amplitude profiles along a single wire 250 and multiple wires 252, 254, 256. In FIG. 2G each amplitude profile was normalized to the peak value. The axial resolutions of the DAS and UBP (465 μm) are almost three times worse than that of SPANNER and MBR (165 μm). While the MBR was more successful in rejecting the background noise compared to the UBP, the SPANNER markedly outperforms all algorithms and significantly reduces the background noise by at least 40 dB (an order of magnitude better than DAS). FIG. 2H illustrates the separability of multiple point targets using the amplitude profiles through the three tightly packed wires (~1 mm apart) 252, 254, 256. The DAS failed to detect the center point target, whereas the UBP, MBR, and SPANNER resolved all three distinct points. The SPANNER and MBR retained a markedly better axial resolution in contrast to the DAS and UBP. However, the MBR algorithm, while outperforming the DAS and UBP, generated multiple spurious artifacts that prevented proper image quantification and reduced the contrast and thus was also limited to a dynamic range of 20 dB or less. The SPANNER provides an additional 15-20 dB of dynamic range and allows a more physically accurate reconstruction.

Figure 3B:
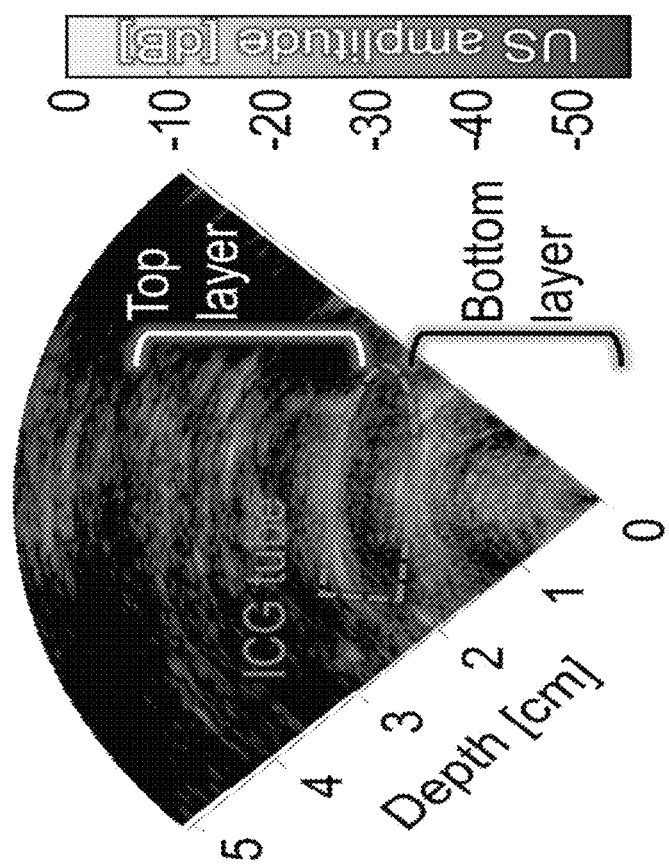
FIG. 3B is a B-mode ultrasound image of the experiment in FIG. 3A.
Figure 3A:
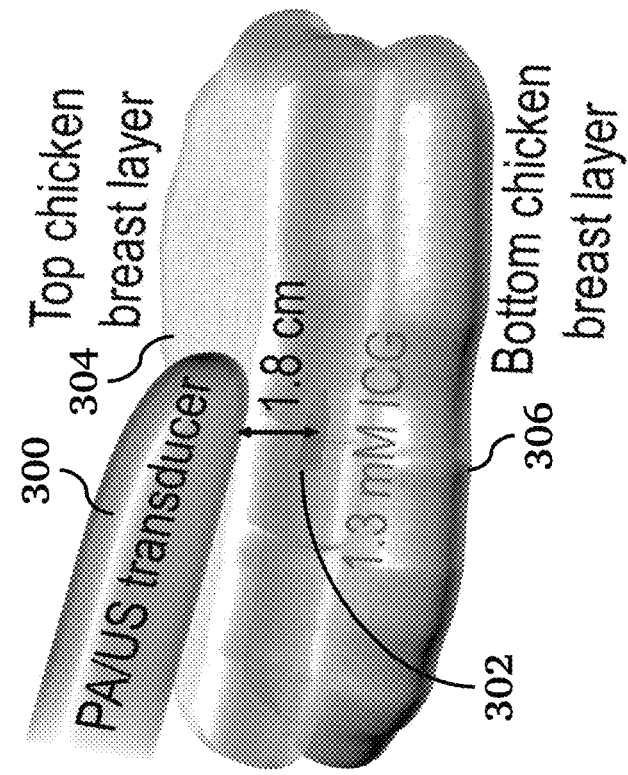
FIG. 3A is a schematic diagram illustrating an experimental setup used for multispectral reconstruction.
Figure 3C:
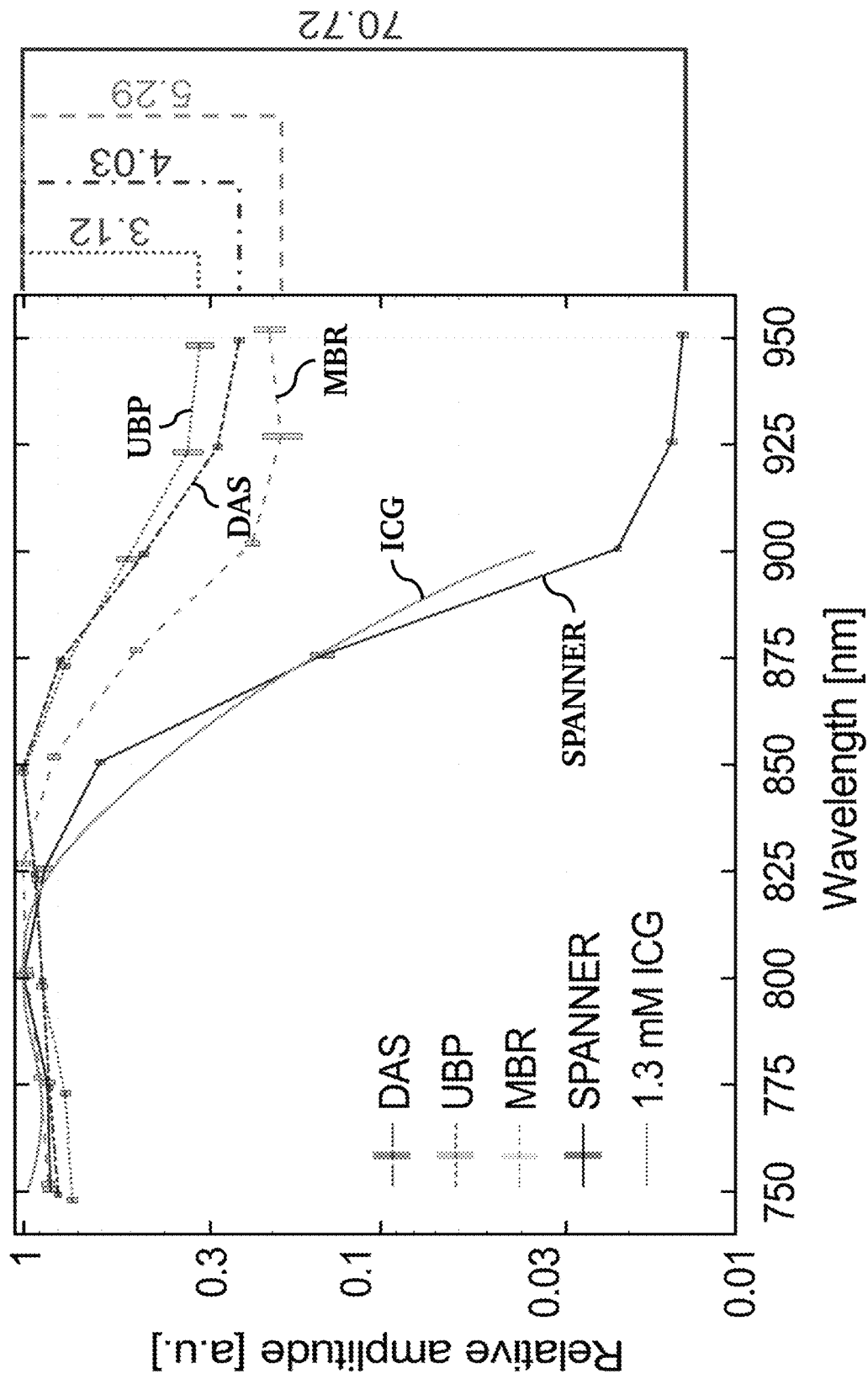
FIG. 3C is a graph showing the DAS, UBP, MBR, and SPANNER PA spectra vs. the actual ICG absorption spectrum.

Experiments were also performed to demonstrate the multispectral performance of the four reconstruction algorithms. FIG. 3A shows the experimental setup where a PA/US transducer 300 is used to image an ICG tube 302 sandwiched between top 304 and bottom 306 chicken breast layers. FIG. 3B is a B-mode ultrasound image confirming the ICG tube positioned between the chicken breast layers. FIG. 3C shows the PA amplitude spectra vs. the actual ICG absorption spectrum using the DAS, UBP, MBR, and SPANNER reconstruction algorithms. The values shown are average across all pixels±95% confidence intervals. The known, normalized absorption spectra of ICG with the same concentration[34] is included as a reference. Both the DAS and UBP algorithms fail to track the ICG spectrum accurately.

Moreover, the dynamic range, i.e., the change in absorption between peak and lowest absorption, is limited to a 3-fold for the UBP and 4-fold for the DAS. The MBR performed slightly better with a dynamic range of 5-fold. In contrast, The SPANNER produces accurate quantitative measurements that correlate well with the ICG absorption spectrum at 1.3 mM. Furthermore, the dynamic range of the SPANNER is more than an order of magnitude better (~71-fold) than all other algorithms.

Ex Vivo Imaging of Pancreatic Cancers

Experiments were also performed to compare ultrasound (US), fluorescence (FL), and photoacoustic (PA) ex vivo images of clinically excised pancreatic cancer samples. The tissue samples were sandwiched between two blocks of agar. The boundary of the pancreatic cancer sample was confirmed by histopathology.

Figure 4B:
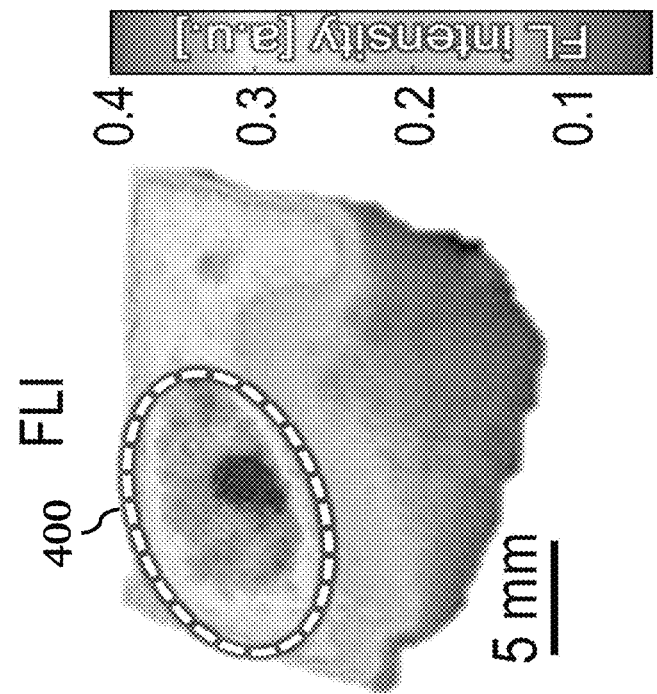
FIG. 4B is a fluorescence heatmap image of a part of the pancreases tissue sample, showing the high signal in the pancreas tumor region.
Figure 4A:
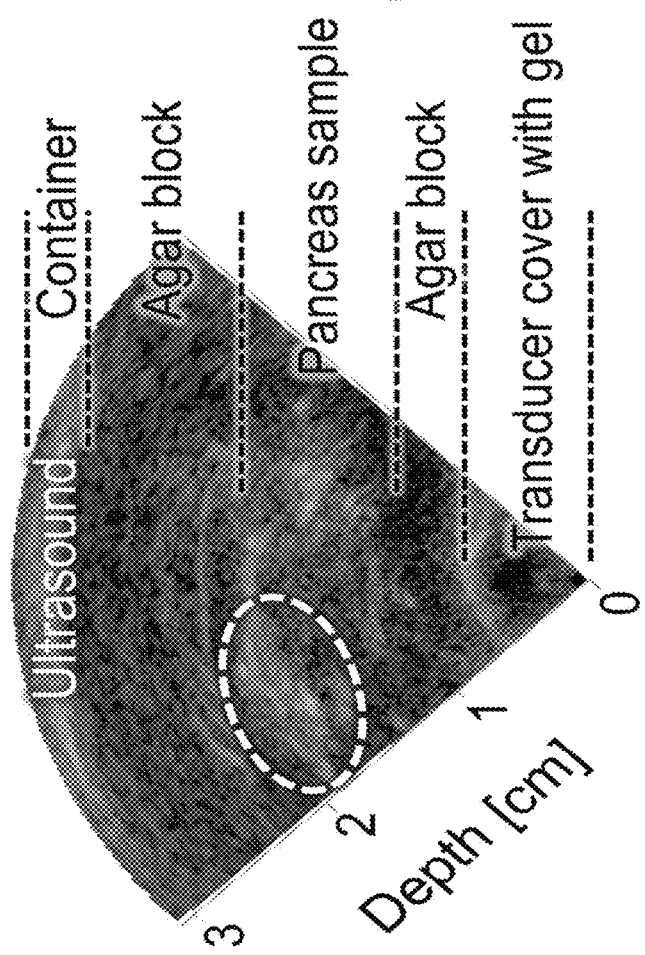
FIG. 4A is a B-mode ultrasound image of a pancreas tissue sample sandwiched between two agar blocks.
Figure 4C:
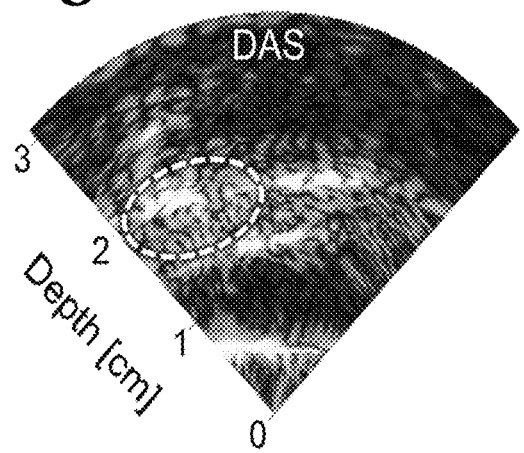
FIGS. 4C, 4D, 4E, 4F are PA images of the same tissue sample produced by the DAS, UBP, MBR, and SPANNER reconstructions, respectively.
Figure 4D:
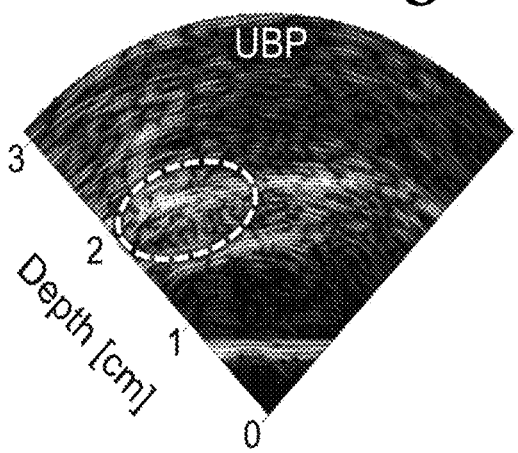
Figure 4E:
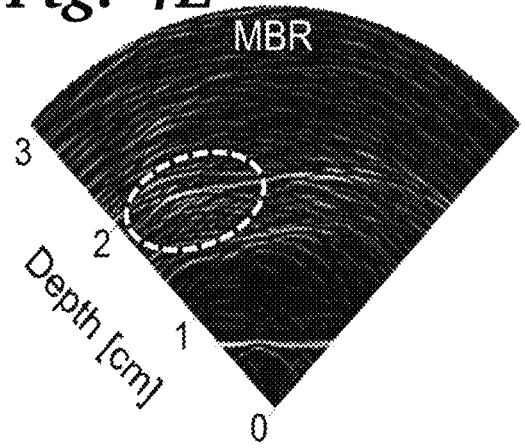
Figure 4F:
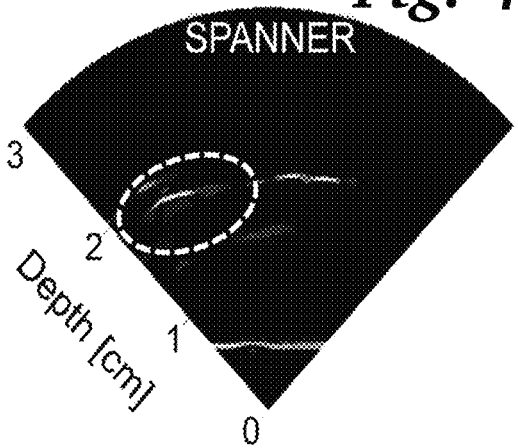

FIG. 4A is a conventional US B-mode image of the tissue sample sandwiched between two agar blocks. FIG. 4B is a FL heatmap of a part of the pancreases tissue sample, showing the high signal in the tumor region. The tissue sample was shown to be highly fluorescent when excited at 780 nm, especially the tumor region 400. FIGS. 4C, 4D, 4E, 4F show PA images of the same tissue sample that were reconstructed by the DAS, UBP, MBR, and SPANNER methods, respectively. The PA images are shown in the log scale with a 40-dB dynamic range. The bright signals were observed at the bottom of each of the PA images, mainly due to the suboptimal acoustic and optical coupling between the gel-filled transducer cover and the agar blocks. Otherwise, all PA reconstruction algorithms were able to detect the FLI contrast agent successfully and showed a good correlation with FLI. As expected, the DAS, UBP, and MBR fail to entirely reject noise and undesired signals from the clear agar blocks surrounding the sample, leading to a 10-fold (20 dB) decrease, in contrast, relative to the SPANNER.

In Vivo Imaging of Prostate Cancers

Figure 5L:
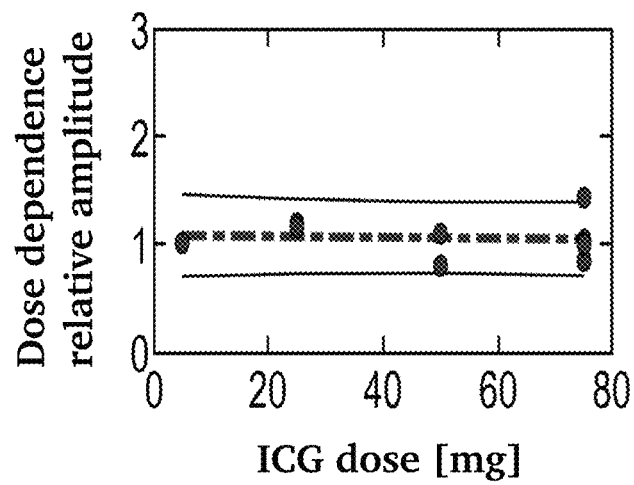
FIG. 5L, 5M, 5N, 5O are graphs of relative PA amplitudes within the prostate (post-injection amplitude divided by pre-injection amplitude) as a function of ICG dose for the DAS, UBP, MBR, and SPANNER algorithms, respectively.
Figure 5M:
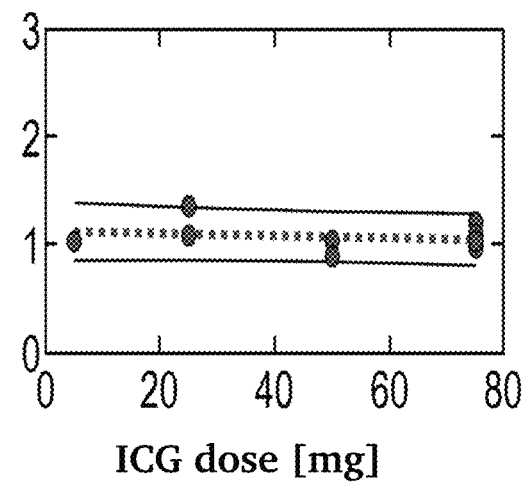
Figure 5N:
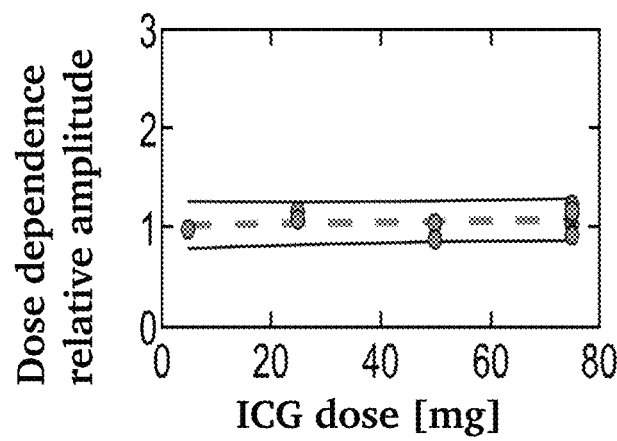
Figure 5O:
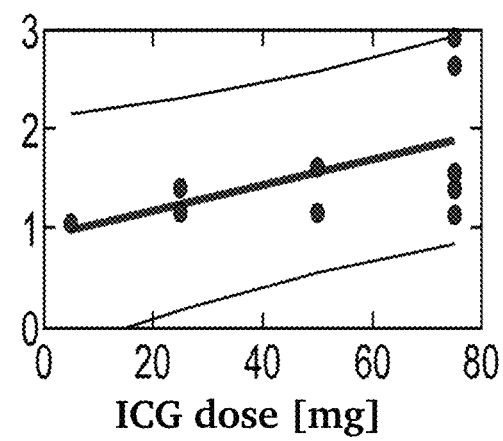

Experiments were also performed to acquire in vivo PAI data from patients with suspected prostate cancer. FIG. 5A shows a B-mode US image for anatomical reference, where rectal wall (R), prostate (P), connective tissue (C), and bladder (B) are delineated with dashed lines.

FIG. 5B shows a graph of quantified PA amplitudes at the prostate regions before and after injection of ICG at 800 nm (N=10). Paired t-test showing that the SPANNER achieved a statistically significant difference (p=0.04). The PA amplitudes estimated with all four algorithms are quantitatively compared before and after the injection of ICG at 800 nm. This wavelength allows the maximal PA signal due to the peak ICG absorption. All methods demonstrated a mean increase in PA amplitude (DAS, 5.4%; UBP, 6.4%; MBR, 6.5%; and SPANNER, 59.5%), but the DAS, UBP, and MBR failed to produce any statistically significant difference (p-values of 0.25, 0.13 and 0.08 respectively). In contrast, the SPANNER was able to demonstrate a statistically significant difference in quantitative PA value before and after injection (p-value<0.04).

To further confirm whether the PA signal increase after ICG injection is attributed to ICG injection, to any intrinsic contrast, or motion artifacts, we analyzed the spectral PA response at another wavelength, 950 nm, where no ICG absorbs light. FIG. 5C shows a graph of quantified PA amplitudes of the prostate before and after injection of ICG at 950 nm (N=8). The SPANNER only generated the PA signals with a full overlap of the confidence intervals, and thus showing statistically significant equivalency between two PA signals before and after injection at 950 nm.

FIGS. 5D, 5E, 5F, 5G show exemplary pre-injection PA images at 800 nm reconstructed using DAS, UBP, MBR, and SPANNER reconstruction methods, respectively. Similarly, FIGS. 5H, 5I, 5J, 5K show exemplary post-injection PA images at 800 nm reconstructed using DAS, UBP, MBR, and SPANNER reconstruction methods, respectively. These PA images are of the same patient immediately after injection of 25 mg of ICG. When comparing a set of exemplary PA images before and after ICG injection, we qualitatively observed a slight increase in PA amplitude between those images reconstructed using the four different algorithms. These differences are further pronounced in the SPANNER images. Further, the background noises are prominent in the DAS, UBP, and MBR images, while the noises are significantly suppressed in the SPANNER image.

FIGS. 5L, 5M, 5N, 5O are plots of relative PA amplitudes at 800 nm within the prostate (post-injection amplitude divided by pre-injection amplitude) as a function of ICG dose for the DAS, UBP, MBR, and SPANNER methods, respectively. Thick lines show linear regression; thin lines show 90% prediction bounds. Since there were only a few patients for each dose (one to five patients per dose), the confidence intervals are broad. Nevertheless, only the SPANNER produces a trend sensitive to the ICG dose.

The slope of SPANNER (12.85 $g^{-1}$ ICG) was 12 to 28 times higher than any other method (−0.46, −1.03, and 1.76 $g^{-1}$ ICG for the DAS, MBR, and UBP respectively).

GPU Implementation of the SPANNER

The GPU implementation was able to reconstruct both PA and US images with a clinically-relevant image grid (5 cm in depth and 4 cm in azimuth with a 135-micron pixel size) in ~90 milliseconds. This reconstruction time includes all overhead, including the transfer of data from Matlab to the GPU and back. For PAI alone, the SPANNER was able to achieve ~45 milliseconds of computation time per frame. Such a rate allows for a frame rate higher than 11 frames per second for combined PAI and USI or 22 frames per second for PAI alone.

Discussion

The SPANNER method for PA image reconstruction is explicitly designed to overcome the existing hurdles for clinically realistic PAI, which include limited viewing angles and high noise, and to enable real-time imaging. The SPANNER method leverages a model-based approach[26] for forward modeling that is combined with the concept of mathematical superiorization[21]. Unlike a simple, conjugate gradient algorithm that solves the linear model matrix equation, the SPANNER method enforces nonnegativity and anisotropic total variation regularization that results in robustness to noise and physically accurate images. The SPANNER method was thoroughly compared with both the DAS and UBP beamforming methods, two of the most widely-used algorithms in biomedical PAI[36]. Additionally, the SPANNER method was also compared to a model-based approach (MBR) using the same forward model matrix as SPANNER but with Tikonov $L^2$ regularization and a conjugate gradient algorithm. Because clinical translation is our primary focus, SPANNER is more compatible with clinical transducers and PA tomography.

Based on the in-silico and in vitro results, the SPANNER method can improve axial resolution by up to 3-fold and contrast by up to an order of magnitude. The SPANNER method provided a more quantitative reconstruction and was shown to quantify the ICG absorption spectrum properly and achieved a 15-30 fold higher dynamic range. Thus, SPANNER represents a significant improvement toward clinical translation of PAI. Applying SPANNER to ex-vivo patient sample data showed a high correlation with fluorescence signals and better rejection of the background. Statistical analysis of in-vivo data showed the improved ability of SPANNER to distinguish between images before and after ICG injection. This will allow for better diagnostic capabilities and reducing the agent dosage.

The SPANNER method has a strong dependence on an accurate forward model matrix. The model matrix used in SPANNER describes the relationship between the image to be estimated and the (noiseless) RF signals to be measured. The model matrix can be calculated in advance and incorporates data regarding the transducer properties and the geometry of imaging. In the description above, we not optimize the speed of sound or acoustic attenuation and instead used standard values from the literature (1540 m/s and 0.5 dB/MHz/cm). The inventors envision that tuning of these values may result in improved images. However, there is low sensitivity to the exact value chosen because errors from the limited view and low SNR overwhelm these inaccuracies. Nevertheless, some inaccuracies in the model matrix may lead to artifacts in image reconstruction. In that regard, the DAS algorithm, and its variants[19], only requires the exact location of each transducer element with respect to each pixel, which is more straightforward to implement. However, the model matrix only needs to be calculated once. Because all the required data needed for the calculation can be collected in advance by simple hydrophone measurements, we do not consider data availability to be a significant hurdle.

While SPANNER can better utilize the raw RF data to form a more accurate image, it does not generate missing data due to the limited viewing angles. A transducer optimized for ultrasound imaging (and especially phased-array where the aperture is typically small) would provide poor PAI regardless of the algorithm used for reconstruction. For example, in the wire-phantom experiments, the axial resolution was improved three-fold with SPANNER, but the lateral resolution was not. The inventors envision that it is preferable to use a transducer array design (such as a large aperture or a concave array) to negate the effects of the limited view[37]. A system fully optimized for PAI, however, sacrifices quality of co-registered USI and clinical applicability.

The SPANNER method makes use of the assumption of nonnegativity. As long as the medium of interest is characterized by a positive Grüneisen coefficient (which is the case for all native tissue components under physiological conditions), a nonnegativity constraint can improve results. However, under certain extreme conditions (such as very low temperatures[38] and for some unusual contrast agents[39]), a negative Grüneisen may be encountered. Under these conditions, the nonnegativity constraint may be removed from the algorithm by a simple modification of the projected estimate, but this can adversely affect the algorithm's performance.

Since SPANNER provides acoustic reconstruction only (i.e., estimation of the initial pressure and not of the actual absorption), compensation of the fluence remains a significant challenge in PAI[32] and, to the best of our knowledge, is not yet addressed by any generalizable algorithm. However, because SPANNER provides a more accurate acoustic reconstruction of the initial pressure compared to other commonly used algorithms, it provides a better starting point to build upon for any further offline analysis that attempts at compensating for the fluence variations.

Lastly, the computation time is vital for the clinical utilization of SPANNER. With a proper implementation on a single GPU, SPANNER can achieve a frame rate greater than 20 frames per second (or ten frames per second combined with high-end USI). Because many Q-switched nanosecond lasers used for deep tissue PAI are limited to 10 pulses per second, this is not a significant hurdle. Moreover, this frame rate is sufficiently fast for many clinical applications. Algorithms like DAS enjoy a simple closed-form structure that allows the calculation of all required parameters during imaging. Thus, it can be adapted to many imaging configurations with no prior preparations. In contrast, SPANNER relies on a forward model matrix that needs to be computed and stored in advance. The offline computation of the model matrix can take at least several hours. Such calculation can be accelerated as well by a proper GPU implementation; moreover, it is only required once per experimental setting. For example, all results in this paper were achieved using only three distinct model matrices: one for the simulation of a 192 element transducer, one for the clinical device in water (wire phantom), and one for the same device in patients (where the speed of sound was set to 1540 m/s). Recent research suggests that the computation of the model matrix might also be performed in real-time during imaging by utilizing some approximations[40], which might allow easier adaptation of SPANNER.

The implications of more quantitative images in-vivo are far-reaching. Clinical translation of PAI has just begun in recent years[18]; however, almost every clinical application that requires an imaging depth of more than a few mm and relies on optical absorption contrast can benefit from the increase in accuracy and lower background levels. Applications like image-guided surgery[41] and visual servoing[42] can immediately benefit from SPANNER to better pinpoint surgical tools and major blood vessels, which is not achievable with the DAS due to his background noise[42]. Moreover, endogenous contrast might not be sufficient to provide clinicians with molecular data related to disease location and progression[43]. Thus, exogenous contrast agents (mostly likely functionalized small molecules), in combination with clinical PAI, can provide a wealth of molecular information with applications for biopsy guidance[44], detection of cancer[45], and triaging[46] as well as monitoring of tumor recurrence and treatment efficacies[47]. The increased sensitivity provided by the SPANNER can help minimize the injected dose required for reliable imaging, potentially reducing any adverse toxicities from the contrast agents and allowing more frequent imaging that can significantly assist in the clinical translation of PAI.

The inventors envision full integration of SPANNER into the clinical imaging workflow. Both the pre-processing Weiner filter and the main algorithm have multiple parameters to control their behavior (such as the number of iterations, tolerance for convergence, and level of noise rejection). The full optimization of those parameters depends on the specific geometry, detector sensitivity, and target to be imaged. The inventors also envision application of the SPANNER algorithm to full 3D tomography. Adaptation of the SPANNER algorithm for 3D applications is straightforward and mainly involves modification of the fast gradient projection[48]. The forward model matrix also is updated. Its memory size might grow considerably (10-100 fold) in such a manner that it may not allow real-time applications. For many clinical applications, a single 2D image or a stack of images that emulate the full 3D data are sufficient, and would involve further investigation[49].

To conclude, this work presents a method for the reconstruction of PA images with markedly better accuracy, resolution, and dynamic range compared to all other algorithms. It is specifically designed for clinical PAI applications in which there is limited viewing angle and low SNR at depth. Real-time application of SPANNER can open avenues for clinical translation of PAI for an abundance of applications.

REFERENCES

[1] P. Beard, "Biomedical photoacoustic imaging," *Interface focus*, vol. 1, no. 4, pp. 602-631, 2011.
[2] G. P. Luke, D. Yeager, and S. Y. Emelianov, "Biomedical applications of photoacoustic imaging with exogenous contrast agents," *Annals of biomedical engineering*, vol. 40, no. 2, pp. 422-437, 2012.
[3] K. Maslov, H. F. Zhang, S. Hu, and L. V. Wang, "Optical-resolution photoacoustic microscopy for in vivo imaging of single capillaries," *Optics letters*, vol. 33, no. 9, pp. 929-931, 2008.
[4] X. Wang, Y. Pang, G. Ku, X. Xie, G. Stoica, and L. V. Wang, "Noninvasive laser-induced photoacoustic tomography for structural and functional in vivo imaging of the brain," *Nature biotechnology*, vol. 21, no. 7, pp. 803-806, 2003.
[5] W. Choi, E.-Y. Park, S. Jeon, and C. Kim, "Clinical photoacoustic imaging platforms," *Biomedical engineering letters*, vol. 8, no. 2, pp. 139-155, 2018.
[6] M. Jeon, J. Kim, and C. Kim, "Multiplane spectroscopic whole-body photoacoustic imaging of small animals in vivo," *Medical & biological engineering & computing*, vol. 54, no. 2-3, pp. 283-294, 2016.
[7] A. P. Jathoul et al., "Deep in vivo photoacoustic imaging of mammalian tissues using a tyrosinase-based genetic reporter," *Nature Photonics*, vol. 9, no. 4, p. 239, 2015.
[8] J. Staley, P. Grogan, A. K. Samadi, H. Cui, M. S. Cohen, and X. Yang, "Growth of melanoma brain tumors monitored by photoacoustic microscopy," *Journal of biomedical optics*, vol. 15, no. 4, p. 040510, 2010.
[9] A. Dima and V. Ntziachristos, "In-vivo handheld optoacoustic tomography of the human thyroid," *Photoacoustics*, vol. 4, no. 2, pp. 65-69, 2016.
[10] I. Stoffels et al., "Metastatic status of sentinel lymph nodes in melanoma determined noninvasively with multispectral optoacoustic imaging," *Science translational medicine*, vol. 7, no. 317, pp. 317ra199-317ra199, 2015.
[11] A. Horiguchi et al., "A pilot study of photoacoustic imaging system for improved real-time visualization of neurovascular bundle during radical prostatectomy," *The Prostate*, vol. 76, no. 3, pp. 307-315, 2016.
[12] J. Aguirre et al., "Precision assessment of label-free psoriasis biomarkers with ultra-broadband optoacoustic mesoscopy," *Nature Biomedical Engineering*, vol. 1, no. 5, p. 0068, 2017.
[13] A. Dima and V. Ntziachristos, "Non-invasive carotid imaging using optoacoustic tomography," *Optics express*, vol. 20, no. 22, pp. 25044-25057, 2012.
[14] K. E. Wilson, T. Y. Wang, and J. K. Willmann, "Acoustic and photoacoustic molecular imaging of cancer," *Journal of Nuclear Medicine*, vol. 54, no. 11, pp. 1851-1854, 2013.
[15] S. Zackrisson, S. Van De Ven, and S. Gambhir, "Light in and sound out: emerging translational strategies for photoacoustic imaging," *Cancer research*, vol. 74, no. 4, pp. 979-1004, 2014.
[16] R. G. Kolkman, P. J. Brands, W. Steenbergen, and T. G. van Leeuwen, "Real-time in vivo photoacoustic and ultrasound imaging," *Journal of biomedical optics*, vol. 13, no. 5, p. 050510, 2008.
[17] K. Daoudi et al., "Handheld probe integrating laser diode and ultrasound transducer array for ultrasound/photoacoustic dual modality imaging," *Optics express*, vol. 22, no. 21, pp. 26365-26374, 2014.
[18] I. Steinberg, D. M. Huland, O. Vermesh, H. E. Frostig, W. S. Tummers, and S. S. Gambhir, "Photoacoustic clinical imaging," *Photoacoustics*, 2019.
[19] S. Jeon, E.-Y. Park, W. Choi, R. Managuli, K. jong Lee, and C. Kim, "Real-time delay-multiply-and-sum beamforming with coherence factor for in vivo clinical photoacoustic imaging of humans," *Photoacoustics*, vol. 15, p. 100136, 2019.
[20] T. L. Szabo, *Diagnostic ultrasound imaging: inside out*. Academic Press, 2004.
[21] Y. Censor, G. T. Herman, and M. Jiang, "Superiorization: theory and applications," *Inverse Problems*, vol. 33, no. 4, p. 040301, 2017.
[22] M. Xu and L. V. Wang, "Universal back-projection algorithm for photoacoustic computed tomography," *Physical Review E*, vol. 71, no. 1, p. 016706, 2005.
[23] C. C. Paige and M. A. Saunders, "LSQR: An algorithm for sparse linear equations and sparse least squares," *ACM Transactions on Mathematical Software (TOMS)*, vol. 8, no. 1, pp. 43-71, 1982.
[24] D. Van de Sompel, L. S. Sasportas, J. V. Jokerst, and S. S. Gambhir, "Comparison of deconvolution filters for photoacoustic tomography," *PloS one*, vol. 11, no. 3, p. e0152597, 2016.
[25] M. V. Zibetti, C. Lin, and G. T. Herman, "Total variation superiorized conjugate gradient method for image reconstruction," *Inverse Problems*, vol. 34, no. 3, p. 034001, 2018.
[26] A. Rosenthal, D. Razansky, and V. Ntziachristos, "Fast semi-analytical model-based acoustic inversion for quantitative optoacoustic tomography," *IEEE transactions on medical imaging*, vol. 29, no. 6, pp. 1275-1285, 2010.
[27] X. L. Deán-Ben, R. Ma, A. Rosenthal, V. Ntziachristos, and D. Razansky, "Weighted model-based optoacoustic reconstruction in acoustic scattering media," *Physics in Medicine & Biology*, vol. 58, no. 16, p. 5555, 2013.
[28] X. L. Deán-Ben, A. Buehler, V. Ntziachristos, and D. Razansky, "Accurate model-based reconstruction algorithm for three-dimensional optoacoustic tomography," *IEEE Transactions on Medical Imaging*, vol. 31, no. 10, pp. 1922-1928, 2012.
[29] J. Jian, L. Han, and X. Jiang, "A hybrid conjugate gradient method with descent property for unconstrained optimization," *Applied Mathematical Modelling*, vol. 39, no. 3-4, pp. 1281-1290, 2015.
[30] S.-R. Kothapalli et al., "Simultaneous transrectal ultrasound and photoacoustic human prostate imaging," *Science translational medicine*, vol. 11, no. 507, p. eaav2169, 2019.
[31] W. S. Tummers et al., "Intraoperative pancreatic cancer detection using tumor-specific multimodality molecular imaging," *Annals of surgical oncology*, vol. 25, no. 7, pp. 1880-1888, 2018.
[32] B. T. Cox, J. G. Laufer, P. C. Beard, and S. R. Arridge, "Quantitative spectroscopic photoacoustic imaging: a review," *Journal of biomedical optics*, vol. 17, no. 6, p. 061202, 2012.
[33] S. Tzoumas, N. C. Deliolanis, S. Morscher, and V. Ntziachristos, "Unmixing molecular agents from absorbing tissue in multispectral optoacoustic tomography," *IEEE transactions on medical imaging*, vol. 33, no. 1, pp. 48-60, 2013.

[34] M. Landsman, G. Kwant, G. Mook, and W. Zijlstra, "Light-absorbing properties, stability, and spectral stabilization of indocyanine green," *Journal of applied physiology*, vol. 40, no. 4, pp. 575-583, 1976.

[35] D. Hyun, Y. L. Li, I. Steinberg, M. Jakovljevic, T. Klap, and J. J. Dahl, "An Open Source GPU-Based Beamformer for Real-Time Ultrasound Imaging and Applications," in *2019 IEEE International Ultrasonics Symposium (IUS)*, 2019: IEEE, pp. 20-23.

[36] A. Rosenthal, V. Ntziachristos, and D. Razansky, "Acoustic inversion in optoacoustic tomography: A review," *Current medical imaging reviews*, vol. 9, no. 4, pp. 318-336, 2013.

[37] M. W. Schellenberg and H. K. Hunt, "Hand-held optoacoustic imaging: A review," *Photoacoustics*, vol. 11, pp. 14-27, 2018.

[38] K. V. Larin, I. Larina, M. Motamedi, and R. Esenaliev, "Optoacoustic laser monitoring of cooling and freezing of tissues," *Quantum Electronics*, vol. 32, no. 11, p. 953, 2002.

[39] E. Petrova, A. Liopo, A. A. Oraevsky, and S. A. Ermilov, "Temperature-dependent optoacoustic response and transient through zero Grüneisen parameter in optically contrasted media," *Photoacoustics*, vol. 7, pp. 36-46, 2017.

[40] L. Ding, X. L. Deán-Ben, and D. Razansky, "20 frames per second model-based reconstruction in cross-sectional optoacoustic tomography," in *Photons Plus Ultrasound: Imaging and Sensing 2017*, 2017, vol. 10064: International Society for Optics and Photonics, p. 100641A.

[41] I. S. Alam et al., "Emerging intraoperative imaging modalities to improve surgical precision," *Molecular Imaging and Biology*, vol. 20, no. 5, pp. 705-715, 2018.

[42] M. A. L. Bell and J. Shubert, "Photoacoustic-based visual servoing of a needle tip," *Scientific reports*, vol. 8, no. 1, pp. 1-12, 2018.

[43] P. J. van den Berg, K. Daoudi, H. J. B. Moens, and W. Steenbergen, "Feasibility of photoacoustic/ultrasound imaging of synovitis in finger joints using a point-of-care system," *Photoacoustics*, vol. 8, pp. 8-14, 2017.

[44] C. Kim et al., "Handheld array-based photoacoustic probe for guiding needle biopsy of sentinel lymph nodes," *Journal of biomedical optics*, vol. 15, no. 4, p. 046010, 2010.

[45] K. S. Valluru, K. E. Wilson, and J. K. Willmann, "Photoacoustic imaging in oncology: translational preclinical and early clinical experience," *Radiology*, vol. 280, no. 2, pp. 332-349, 2016.

[46] J. Kim et al., "Multispectral photoacoustic assessment of thyroid cancer nodules in vivo," in *Photons Plus Ultrasound: Imaging and Sensing 2020*, 2020, vol. 11240: International Society for Optics and Photonics, p. 1124004.

[47] S. Mallidi, K. Watanabe, D. Timerman, D. Schoenfeld, and T. Hasan, "Prediction of tumor recurrence and therapy monitoring using ultrasound-guided photoacoustic imaging," *Theranostics*, vol. 5, no. 3, p. 289, 2015.

[48] A. Beck and M. Teboulle, "Fast gradient-based algorithms for constrained total variation image denoising and deblurring problems," *IEEE transactions on image processing*, vol. 18, no. 11, pp. 2419-2434, 2009.

[49] C. Lee, W. Choi, J. Kim, and C. Kim, "Three-dimensional clinical handheld photoacoustic/ultrasound scanner," *Photoacoustics*, p. 100173, 2020.

The invention claimed is:

1. A method for photoacoustic imaging comprising:
measuring radiofrequency (RF) time samples from transducer elements wherein the transducer elements are arranged in a 3D shape;
reconstructing an estimated initial pressure image from the measured RF time samples and a pre-calculated forward model matrix wherein the pre-calculated forward model matrix takes into account the arrangement of the 3D shape;
wherein reconstructing comprises minimizing the difference between the pre-calculated forward model matrix applied to the estimated initial pressure image and the measured RF time samples by implementing a superiorized modified conjugate gradient least squares algorithm to minimize the total variation norm;
wherein the pre-calculated forward model matrix factors each of the transducer elements into sub-wavelength mathematical elements.

2. The method of claim 1 wherein the pre-calculated forward model matrix accounts for individual element sensitivity and includes data regarding each element's directivity and shape.

3. The method of claim 1 wherein reconstructing the estimated initial pressure image is implemented in parallel on a GPU.

4. The method of claim 1 wherein reconstructing the estimated initial pressure image uses a hybrid coefficient to incorporate computed data from previous iterations to accelerate a next iteration.

5. The method of claim 1 wherein reconstructing the estimated initial pressure image incorporates data from previous reconstructed images as an initial guess to accelerate the reconstruction of the next image.

6. The method of claim 1 wherein columns of the pre-calculated forward model matrix columns are normalized.

7. The method of claim 1 wherein the pre-calculated forward model matrix is computed and stored in advance.

* * * * *